United States Patent [19]
Richey, Jr. et al.

[11] Patent Number: 5,112,984
[45] Date of Patent: May 12, 1992

[54] PROCESSES FOR THE PREPARATION OF CYCLIC NITROGEN-CONTAINING COMPOUNDS

[75] Inventors: Forrest A. Richey, Jr.; Arthur R. Doumaux, Jr., both of Charleston, W. Va.

[73] Assignee: Union Carbide Chemicals & Plastics Technology Corporation, Danbury, Conn.

[21] Appl. No.: 585,458

[22] Filed: Sep. 20, 1990

[51] Int. Cl.$^5$ ............................................. C07D 233/34
[52] U.S. Cl. ....................................... 548/320; 568/876
[58] Field of Search ................................. 548/300, 320

[56] References Cited

U.S. PATENT DOCUMENTS

| | | | |
|---|---|---|---|
| 2,517,750 | 8/1950 | Wilson | 548/300 |
| 2,812,333 | 11/1957 | Steele | 548/300 |
| 3,876,657 | 4/1975 | Aelony et al. | 548/300 |
| 3,910,948 | 10/1975 | Mod et al. | 548/300 |
| 4,405,794 | 9/1983 | Harnden et al. | 548/229 |
| 4,511,722 | 4/1985 | Krimm et al. | 548/231 |
| 4,642,351 | 2/1987 | Woo et al. | 548/317 |
| 4,668,793 | 5/1987 | Nagata et al. | 548/317 |
| 4,731,453 | 3/1988 | Nagata et al. | 548/317 |

OTHER PUBLICATIONS

Shenoy, P. K. et al., American Dyestuff Reporter, May 6, 1968, pp. 17–34.
Nomura, R. et al., Ind. Eng. Chem. Res., 1987, 26, pp. 1056–1059.
Enichem Synthesis SpA, Dimethyl Carbonate Product Bulletin, p. 13, (1975).
Dow Chemical U.S.A., Experimental Ethylene Carbonate XAS-1666.00L Product Bulletin (1982), p. 7.
Texaco Chemical Company, TEXACAR® Ethylene and Propylene Carbonates Product Bulletin (1987), p. 24.

Primary Examiner—Joseph Paul Brust
Attorney, Agent, or Firm—Rose M. Allen

[57] ABSTRACT

A process for preparing cyclic nitrogen-containing compounds which comprises contacting an acyclic nitrogen-containing compound with a $CO_2$ synthon at an elevated temperature for a period of time sufficient to produce the cyclic nitrogen-containing compound.

1 Claim, No Drawings

PROCESSES FOR THE PREPARATION OF CYCLIC NITROGEN-CONTAINING COMPOUNDS

RELATED APPLICATIONS

The following are related, commonly assigned applications, filed on an even date herewith: U.S. patent application Ser. No. 07,585,560; and U.S. patent application Ser. No. 07,585,558; both of which are incorporated herein by reference.

BRIEF SUMMARY OF THE INVENTION

Technical Field

This invention relates to a process for preparing cyclic nitrogen-containing compounds which comprises contacting an acyclic nitrogen-containing compound with a $CO_2$ synthon at an elevated temperature for a period of time sufficient to produce the cyclic nitrogen-containing compound.

BACKGROUND OF THE INVENTION

Various processes for the production of imidazolidinones (ethylene ureas) are known. Shenoy, P.K. et al., American Dyestuff Reporter, May 6, 1968, pp. 17-34 (352-369), discloses a variety of processes for the preparation of ethylene urea (2-imidazolidinone) and derivatives of ethylene urea. At page 18 (353), it is stated that aminoethylethanolamine and urea can be reacted at a temperature of 100° C.-180° C. to give N-(2-hydroxyethyl)ethyleneurea. Also, at page 18 (353), it is stated that N-(2-hydroxyethyl)ethyleneurea can be prepared from the reaction of aminoethylethanolamine and diethyl carbonate. At page 19 (354), it is stated that N,N'-(dimethyl)ethyleneurea can be prepared by reacting ethylene urea with formaldehyde followed by catalytic hydrogenation with a nickel catalyst, or by using formaldehyde-formic acid reduction of ethylene urea.

U.S. Pat. No. 2,812,333 describes a process for the production of N-(2-hydroxyethyl)ethylenediamine by reacting 2-aminoethanol and carbon dioxide at an elevated temperature and pressure to yield N-(2-hydroxyethyl)ethyleneurea which is hydrolyzed to form N-(2-hydroxyethyl)ethylenediamine.

U.S. Pat. No. 4,731,453 relates to a Process of producing 1,3-dialkyl-2-imidazolidinones directly from N,N'-dialkylethylenediamine and urea which comprises reacting a N,N'-dialkylethylenediamine with urea at a temperature of 180° C. or higher in the presence of a polar solvent to obtain a 1,3-dialkyl-2-imidazolidinone.

U.S. Pat. No. 4,511,722 exemplifies the Preparation of N-(2-hydroxyethyl)ethyleneurea by reacting aminoethylethanolamine and urea at a temperature of 90° C. to 230° C. until the elimination of ammonia is complete.

U.S. Pat. No. 2,517,750 discloses the preparation of imidazolidinones (ethylene ureas). In particular, Example 9 thereof demonstrates the preparation of N-(2-hydroxyethyl)ethyleneurea by reacting aminoethylethanolamine and urea at a temperature of 200° C.

U.S. Pat. No. 4,668,793 describes a process for producing 1,3-dimethyl-2-imidiazolidinone which comprises reacting N,N'-dimethylethylenediamine and/or its hydrochloride with phosgene in the presence of a substantial amount of water and a dehydrochlorinating agent.

U.S. Pat. No. 3,876,657 relates to a method for the preparation of 1-substituted-2-imidazolidinones wherein a tertiary amine monoimide is thermolytically rearranged to provide the 1-substituted-2-imidazolidinone.

U.S. Pat. No. 3,910,948 discloses the preparation of 1,3-diacyl imidazolidinones and hexahydropyrimidines by the reaction of formaldehyde and an N,N'-alkylenebisamide in the presence of a strong acid catalyst, the substituent acyl groups being acetyl, butyryl, pentanoyl, hexanoyl, heptanoyl, octanoyl, nonanoyl, decanoyl, palmitoyl, stearoyl and oleoyl.

U.S. Pat. No. 4,405,794 describes a method for reacting urea and beta-hydroxyethylcarbamate to make 2-oxazolidinone and ethyleneurea whereby the reaction method can be controlled to provide either the 2-oxazolidinone or the ethyleneurea as the major reaction product.

U.S. Pat. No. 4,642,351 relates to a process for the preparation of N-substituted imidazolidinones and N-substituted 2-thionimidazolidinones which comprises contacting an oxazolidinone with a compound containing a nitrogen directly bonded to a carbonyl or a thiocarbonyl group in the presence of a Lewis acid catalyst or the hydrate of a Lewis acid catalyst under conditions such that an N-substituted imidazolidinone or N-substituted 2-thionimidazolidinone is prepared.

Nomura, R. et al., Ind. Eng. Chem. Res., 1987, 26, pp. 1056-1059, discloses the preparation of cyclic ureas from carbon dioxide and diamines catalyzed by triphenylstibine oxide.

Enichem Synthesis Spa, Dimethyl Carbonate Product Bulletin, p. 13, discloses the preparation of imidazolidin-2-ones from ethylenediamines and dimethyl carbonate in the presence of sodium alkoxide.

Dow Chemical U.S.A., Experimental Ethylene Carbonate XAS-1666.00L Product Bulletin (1982), p. 7, describes the condensation reaction of urea and ethylene carbonate to afford imidazolidinones with carbon dioxide and water as by-products. Also, the reaction of ethylene carbonate and diamines, e.g., ethylenediamine, at high temperatures, i.e., 188° C.-200° C., to produce imidazolidinones is disclosed. At lower temperatures, it is stated that dicarbamates result from the reaction of diamines and ethylene carbonate.

Texaco Chemical Company, TEXACAR ® Ethylene and Propylene Carbonates Product Bulletin (1987), p. 24, discloses the preparation of ethylene urea by reacting ethylene carbonate and urea in an autoclave at temperatures around 200° C. followed by heating with water.

DISCLOSURE OF THE INVENTION

This invention relates to a process for Preparing cyclic nitrogen-containing compounds which comprises contacting an acyclic nitrogen-containing compound with a $CO_2$ synthon at an elevated temperature for a period of time sufficient to produce the cyclic nitrogen-containing compound.

This invention also relates to a process for preparing cyclic nitrogen-containing compounds which comprises contacting an acyclic nitrogen-containing compound with an alkylene carbonate at an elevated temperature for a period of time sufficient to produce the cyclic nitrogen-containing compound.

This invention further relates to a process for preparing N-(2-hydroxyethyl)ethyleneurea and ethylene glycol which comprises contacting aminoethylethanolamine with ethylene carbonate at an elevated temperature for a period of time sufficient to produce N-(2-hydroxyethyl)ethyleneurea.

In a preferred embodiment, an alkylene carbonate is employed as the $CO_2$ synthon to selectively provide a cyclic nitrogen-containing compound and an alkylene glycol as co-products of the reaction.

The cyclic nitrogen-containing compounds produced in accordance with the processes of this invention are useful for a wide variety of applications such as solvents, corrosion inhibitors, textile finishing agents, agricultural chemicals, pharmaceutical products, liquid absorbents, polyurethane catalysts and the like.

For purposes of this invention, the term "$CO_2$ synthon" embraces $SO_2$ synthons such as sulfurous acids and sulfurous acid esters.

DETAILED DESCRIPTION

As indicated above, this invention relates to a process for preparing cyclic nitrogen-containing compounds which comprises contacting an acyclic nitrogen-containing compound with a $CO_2$ synthon at an elevated temperature for a period of time sufficient to produce the cyclic nitrogen-containing compound.

As also indicated above, this invention relates to a process for preparing cyclic nitrogen-containing compounds which comprises contacting an acyclic nitrogen-containing compound with an alkylene carbonate at an elevated temperature for a period of time sufficient to produce the cyclic nitrogen-containing compound.

As further indicated above, this invention relates to a process for preparing N-(2-hydroxyethyl)ethyleneurea and ethylene glycol which comprises contacting aminoethylethanolamine with ethylene carbonate at an elevated temperature for a period of time sufficient to produce N-(2-hydroxyethyl)ethyleneurea and ethylene glycol.

As yet further indicated above, in a preferred embodiment, an alkylene carbonate is employed as the $CO_2$ synthon to selectively provide a cyclic nitrogen-containing compound and an alkylene glycol as co-products of the reaction.

Suitable acyclic nitrogen-containing compound starting materials which can be employed in the processes of this invention include any permissible substituted or unsubstituted acyclic nitrogen-containing compound(s). Preferred acyclic nitrogen-containing compound starting materials include aminoethylethanolamine, ethylenediamine, propylenediamine, N,N'-(dimethyl)ethylenediamine and the like. Illustrative acyclic nitrogen-containing compound starting materials useful in this invention include, for example, aminoethylethanolamine, ethylenediamine, propylenediamine, N,N'-(dimethyl)ethylenediamine and the like. The molar ratio of acyclic nitrogen-containing compound to $CO_2$ synthon is not narrowly critical and can range from about 0.05:1 or less to about 50:1 or greater, preferably from about 0.1:1 to about 10:1.

Suitable $CO_2$ synthon starting materials which can be employed in the step (i) transesterification reaction include any permissible substituted or unsubstituted carboxyl-containing compound(s) or carbonyl-containing compound(s) which are capable of reacting with an acyclic nitrogen-containing compound under the process conditions described herein, such as those embraced by the formulae $R_1C(O)R_2$ or $R_1S(O)R_2$ wherein $R_1$ is hydrogen, halogen, amino, hydroxyl or the residue of an organic compound, and $R_2$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, ethylene carbonate, propylene carbonate and the like. The use of $CO_2$ synthons prepared in situ such as the reaction of ethylene glycol and dimethyl carbonate to give ethylene carbonate is encompassed within the scope of this invention.

As indicated above, $R_1$ and $R_2$ can be the residue of an organic compound. Illustrative residues of organic compounds include, for example, alkyl, aryl, alkylamino, arylamino, cycloalkyl, heterocycloalkyl, alkyloxy, aryloxy, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_1$ and $R_2$ substituents together can complete a cycloalkyl ring or a heterocycloalkyl ring which can be substituted or unsubstituted. The $R_1C(O)R_2$ formula is also contemplated to embrace carbon dioxide and carbon monoxide.

A catalyst may optionally be employed in this invention. Permissible catalysts include, for example, basic metal oxides, alkoxides and other basic metal salts such as sodium ethoxide, triphenylantimony oxide and the like. Tertiary amines may also be useful catalysts. The catalyst employed in this invention may also contain support(s), binding agent(s) or other additives to stabilize or otherwise help in the manufacture of the catalyst. Both homogeneous and heterogeneous catalysts can be employed in this invention. The amount of catalyst used is dependent on the particular catalyst employed and can range from about 0.01 weight percent or less to about 10 weight percent or greater of the total weight of the starting materials.

The processes of this invention can be conducted over a wide range of pressures ranging from atmospheric or subatmospheric pressures to superatmospheric pressures. However, the use of very high pressures has not been observed to confer any significant advantages but increases equipment costs. The reaction may be effected in the liquid or vapor or supercritical states or mixtures thereof.

The temperature of the reaction may be as low as about ambient temperature to about 300° C. Preferably, the reaction temperature ranges from about 125° C. to about 250° C., and most preferably from about 150° C. to about 225° C. Reaction temperatures below about 180° C. can be employed in the processes of this invention.

The reaction can be conducted in the presence of an inert diluent which can be either a liquid or gas. When a liquid diluent is employed, it should preferably be a good solvent for the starting materials, inert under the reaction conditions, and of such a nature that separation from the cyclic nitrogen-containing compound product will not be difficult. For instance, the boiling points of the diluent and the cyclic nitrogen-containing compound product should differ by an adequate amount and there should be no tendency of the diluent to form an azeotrope with the desired cyclic nitrogen-containing compound product.

Examples of useful liquid diluents that meet the foregoing qualifications include ethylene glycol, benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired cyclic nitrogen-containing compound products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the cyclic nitrogen-containing product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

The processes of this invention are useful for preparing substituted or unsubstituted cyclic nitrogen-containing compounds. Illustrative cyclic nitrogen-containing compounds prepared by the processes of this invention include, for example, 2-imidazolidinones or ethylene ureas. Illustrative cyclic nitrogen-containing compounds prepared by the processes of this invention include, for example, N-(2-hydroxyethyl)ethyleneurea, propyleneurea, ethyleneurea, N,N'-(dimethyl)ethyleneurea, 5- or 6-membered ring cyclic ureas and the like.

Illustrative of suitable cyclic nitrogen-containing compounds which can be prepared by the processes of this invention include those permissible cyclic nitrogen-containing compounds, including any permissible derivatives of described cyclic nitrogen-containing compounds, which are described in Kirk-Othmer, Encyclopedia of Chemical Technology, Third Edition, 1984, the pertinent portions of which are incorporated herein by reference. Other suitable cyclic nitrogen-containing compounds which can be prepared by the processes of this invention are described in Shenoy, P.K. et al., supra, the disclosure of which is incorporated herein by reference.

The cyclic nitrogen-containing compound products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials at an elevated temperature. When complete conversion is not desired or not obtainable, the starting materials can be separated from the cyclic nitrogen-containing compound product, for example by distillation, and the starting materials then recycled back into the reaction zone.

The processes are conducted for a period of time sufficient to produce the cyclic nitrogen-containing compound products. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the process of this invention include by way of example:

AEEA—aminoethylethanolamine
DEDA—N,N'-(dimethyl)ethylenediamine
PDA—propylenediamine
EC—ethylene carbonate
EDA13 ethylenediamine
PC—propylene carbonate Illustrative of suitable products prepared by the process of this invention include by way of example:

HEEU—N—(2-hydroxy ethyl)ethyleneurea
DMEU—N,N'-(dimethyl)ethyleneurea
PU—propyleneurea
EU—ethyleneurea
EG—ethylene glycol Illustrative of permissible reactions encompassed within the scope of this invention include, for example, the following reactant/product combinations:

| REACTANT(S) | PRODUCT(S) |
| --- | --- |
| AEEA, EC | HEEU, EG |
| DEDA, EC | DMEU |
| PDA, EC | PU |
| EDA, EC | EU |

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxyalkyl, hydroxyalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and hetrocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

The following example is provided to further illustrate the processes of this invention.

EXAMPLE 1

Preparation of N-(2-Hydroxyethyl)ethyleneurea

Into a 25-milliliter round bottom reaction flask equipped with a thermometer and magnetic stirrer was added 10.52 grams (0.10 mole) of aminoethylethanolamine and 8.81 grams (0.10 mole) of ethylene carbonate. The contents were heated from ambient temperature to a maximum temperature of 203° C. during a total time period of 4.25 hours. Analysis by gas chromatography showed complete conversion to N-(2-hydroxyethyl)ethyleneurea and ethylene glycol.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

We claim:

1. A process for preparing N-(2-hydroxyethyl)ethyleneurea and ethylene glycol which comprises contacting aminoethylethanolamine with ethylene carbonate at an elevated temperature for a period of time sufficient to produce N-(2-hydroxyethyl)ethyleneurea and ethylene glycol.

* * * * *